United States Patent [19]

Seyfried et al.

[11] 4,021,555
[45] May 3, 1977

[54] PHARMACEUTICAL PREPARATION AND METHOD FOR TREATMENT OF PARKINSONISM

[75] Inventors: Christoph Seyfried; Herbert Nowak, both of Darmstadt, Germany

[73] Assignee: Merck Patent Gesellschaft mit beschrankter Haftung, Darmstadt, Germany

[22] Filed: Dec. 16, 1975

[21] Appl. No.: 641,350

[30] Foreign Application Priority Data

Mar. 29, 1975 Germany ......................... 2513940

[52] U.S. Cl. ................. 424/250; 424/319

[51] Int. Cl.² ............... A61K 31/20; A61K 31/495
[58] Field of Search ........................... 424/250, 319

[56] References Cited

UNITED STATES PATENTS 3,632,778  1/1972  Sheth .................. 424/319

*Primary Examiner*—Stanley J. Friedman
*Attorney, Agent, or Firm*—Millen & White

[57] ABSTRACT

Administration of mepiprazole during L-dopa therapy for parkinsonism reduces undesired side effects of L-dopa and enhances the desired effects of L-dopa.

8 Claims, No Drawings

PHARMACEUTICAL PREPARATION AND METHOD FOR TREATMENT OF PARKINSONISM

BACKGROUND OF THE INVENTION

This invention relates to a process for modifying the effects of therapeutic administration of L-dopa, and to pharmaceutical preparations suitable for this purpose.

L-Dopa (L-3,4-dihydroxyphenylalanine) is used for the treatment of parkinsonism and Parkinson's disease. The cause of parkinsonism is thought to be a deficiency of the neurotransmitter dopamine, 2-(3,4-dihydroxyphenyl)-ethylamine, in the basal ganglia. Dopamine itself does not pass through the blood-brain barrier; for this reason, this compound is unsuitable for parkinsonism therapy. Consequently, treatment of parkinsonism is carried out by substitute therapy using high doses of L-dopa, a precursor of dopamine, which passes the blood-brain barrier. However, L-dopa is also a precursor of noradrenaline, so that its administration to a patient results in increased formation of noradrenaline. As a result, the metabolic equilibrium of the neurotransmitters noradrenaline and serotonin is disturbed in the brain.

Administration of L-dopa also leads to reduction in the activity of serotoninergic neurons. The result is agitation, motoric unrest, increased sexuality, insomnia, hypomanic reactions, and sometimes even hallucinations and delirious conditions, i.e., L-dopa psychosis. These psychic disturbances normally cannot be overcome by conventional psychopharmacological agents, which simultaneously counteract the effect of the dopamine so that symptoms of the original parkinsonism returns.

It has been found that the psychopharmacological agent mepiprazole, 3-[2-(N'-m-chlorophenyl-piperazino)-ethyl]-5-methylpyrazole, unlike other psychopharmaceuticals, has specific dopamine- and serotonin-potentiating activity and simultaneously has noradrenaline-blocking activity in the central nervous system. Thus, for example, dopamine reuptake according to Carlsson et al., Europ.J.Pharmacol. 5: 367 [1969], was inhibited by 50-70% in rats by administration of 20 mg./kg. of mepiprazole.

The turnover rate of transmitters in rats by the method of Andén et al., Metabolism of Amines in the Brain, Ed., G. Hooper, Macmillan 1969, p. 44, showed a reduction in serotonin turnover of about 50% and an increase in noradrenaline turnover by 60% following administration of 2.5 mg./kg. of mepiprazole. This combination of effects has not been observed heretofore in psychopharmaceuticals. These newly-found properties of mepiprazole permit normalization of noradrenaline and serotonin transmitter metabolism disturbed by the administration of L-dopa, that is, psychic side effects of L-dopa therapy are positively affected and the primary effect of dopamine is enhanced.

The preparation and certain pharmacological properties and medicinal uses of mepiprazole are disclosed in U.S. Pat. No. 3,491,097, incorporated herein by reference. Mepiprazole has for example, narcosis-potentiating effects typical of conventional psychopharmaceuticals. The properties of mepiprazole which are utilized in this invention could not be predicted from the properties set forth in the above reference. Based on the properties indicated in that reference, mepiprazole should have no advantages over other neuroleptics, in L-dopa therapy.

SUMMARY OF THE INVENTION

In a method-of-use aspect, this invention relates to a method of reducing undesirable side effects and/or enhancing the beneficial effects of L-dopa in therapy employing L-dopa comprising administering an amount of mepiprazole or a physiologically and pharmacologically acceptable acid addition salt thereof during such therapy, effective to either enhance the beneficial effects or reduce undesirable side effects of L-dopa therapy, or both. In a preferred embodiment, the mepiprazole and L-dopa are administered as a mixture in unit dosage form, in admixture with a pharmacologically acceptable carrier.

In a composition aspect, this invention relates to a pharmaceutical composition comprising a mixture of an amount per unit dosage of L-dopa effective to ameliorate the symptoms of parkinsonism and an amount per unit dosage of mepiprazole or a physiologically and pharmacologically acceptable acid addition salt thereof, effective to enhance the beneficial effects or reduce undesired side effects of the L-dopa, or both, in admixture with a pharmacologically acceptable carrier.

DETAILED DESCRIPTION

Mepiprazole or its physiologically and pharmacologically acceptable acid addition salts are administered in addition to L-dopa. The dosage can be given in separate pharmaceutical preparations or in combination.

Mepiprazole and its physiologically acceptable acid addition salts are utilized in a mixture with solid, liquid and/or semiliquid excipients customary in the human or veterinary medicine. Suitable carrier substances are organic or inorganic compounds suitable for enteral or parenteral application and which do not react with the effective agents, for example, water, vegetable oils, benzyl alcohols, polyethylene glycols, gelatin, lactose, amylose, magnesium stearate, or talc. Suitable for enteral application are, for example, tablets, dragees, capsules, syrups, elixirs, drops, or suppositories. For parenteral administration, especially suitable are solutions, preferably oily or aqueous solutions, furthermore, suspensions, emulsions, or implants. The effective agents can also be lyophilized and the thus-obtained lyophilized products can be used, for example, for the preparation of injection formulations. The indicated preparations can be sterilized and/or can contain auxiliary agents, such as lubricants, preservatives, stabilizers and/or wetting agents, emulsifiers, salts for influencing the osmotic pressure, buffers, coloring, flavoring and/or aromatous substances. They can, if desired, also contain one or more additional active agents, e.g., vitamins and/or preferably, peripheral decarboxylase inhibitors, e.g., carbidopa, (—)-L-α-hydrazino-3,4-dihydroxy-α-methylhydrocinnamic acid monohydrate, or benserazide, 1-DL-seryl-2-(2,3,4-trihydroxybenzyl)-hydrazine. By incorporating such peripheral decarboxylase inhibitors, the total dose of L-dopa can be lowered further and peripheral side effects can thus be reduced.

The unit dosage of mepiprazole and its physiologically acceptable acid addition salts is dependent on the amount of L-dopa being administered. Normally, about 0.1 – 2% by weight of the administered L-dopa dose of mepiprazole is given. Since L-dopa is normally given in daily dosages of from about 500 to 6000 mg., the required dosage of mepiprazole is about 5 – 20 mg. daily, the proportion for a dosage unit being from 0.5 to 20 mg., preferably from 1 to 5 mg. As is the case for the optimum dose of L-dopa, the optimum dose of mepiprazole must be determined for each individual case. Due to the dopamine-potentiating properties of mepiprazole, the dose of L-dopa required for therapy can be reduced. Oral administration is preferred, especially in the case of combination preparations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Tablets

A mixture of 1 kg. of mepiprazole, 4 kg. of lactose, 1.2 kg. of corn starch, 0.2 kg. of talc, and 0.1 kg. of magnesium stearate is compressed to tablets in the usual way, so that each tablet contains 5 mg. of active agent.

These tablets are administered in addition to the customary preparations which contain L-dopa, so that the weight ratio of L-dopa to mepiprazole is about 100 : 1. The daily dosage is between 1 and 3 tablets.

EXAMPLE 2

Dragees

Analogously to Example 1, dragee cores are produced by a compressing step and are then coated in the usual way with a coating of cane sugar, potato starch, talc, tragacanth, and coloring agent. These dragees are administered in the same manner as the tablets set forth in Example 1.

EXAMPLE 3

Capsules 5 kg. of mepiprazole dihydrochloride is filled as usual in hard gelatin capsules so that each capsule contains 2 mg. of the active agent. The capsules are administered in addition to the customary preparations which contain L-dopa.

EXAMPLE 4

Tablets (Combination Preparation)

5 kg. of L-dopa, 10 g. of mepiprazole dihydrochloride, 20 kg. of lactose, 5 kg. of potato starch, 1 kg. of talc, and 0.5 kg. of magnesium stearate are mixed together and tablets are compressed from the mixture in the usual manner, containing respectively 500 mg. of L-dopa and 1 mg. of mepiprazole dihydrochloride. Daily, 4–8 of these tablets are administered, so that the daily dosage ranges between 2 and 4 g. of L-dopa and between 4 and 8 mg. of mepiprazole dihydrochloride.

EXAMPLE 5

Tablets (Combination Preparation)

2 kg. of L-dopa, 0.5 kg. of benserazide hydrochloride, 10 g. of mepiprazole dihydrochloride, 20 kg. of lactose, 5 kg. of wheat starch, 1 kg. of talc, 0.5 kg. of magnesium stearate, and 1 kg. of cellulose powder are mixed together. Tablets are compressed from the mixture in the usual way, so that each individual tablet contains 200 mg. of L-dopa, 50 mg. of benserazide hydrochloride, and 1 mg. of mepiprazole dihydrochloride. Six to eight of these tablets are administered daily. Accordingly, the daily dosage is 1.2 – 1.6 g. of L-dopa, 0.3 – 0.4 g. of benserazide, and 6 – 8 mg. of mepiprazole dihydrochloride.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising in unit dosage form an amount of L-dopa effective to alleviate the symptoms of parkinsonism and a dosage of mepiprazole or a pharmacologically acceptable acid addition salt thereof, effective to reduce undesired side effects of the amount of L-dopa, in admixture with a pharmacologically acceptable carrier.

2. The composition of claim 1, wherein the amount per unit dosage of mepiprazole is 0.1 – 2% by weight of L-dopa per unit dosage.

3. The composition of claim 1, wherein the amount of mepiprazole per unit dosage is from 0.5 to 20 mg.

4. A method for enhancing the beneficial effects, for reducing the undesirable effects, or for both enhancing the beneficial effects and reducing the undesirable effects of therapy with L-dopa in the treatment of parkinsonism comprising administering during said therapy an amount of mepiprazole or a pharmacologically acceptable salt thereof, effective to enhance said beneficial effects, to reduce said side effects, or to both enhance said beneficial effects and to reduce said side effects.

5. The method of claim 4, wherein the mepiprazole and L-dopa are administered as a mixture in unit dosage form.

6. The method of claim 4, wherein L-dopa and mepiprazole are administered orally.

7. The method of claim 4, wherein the daily dosage of L-dopa is from 500 to 6000 mg. and the daily dosage of mepiprazole is 0.1 – 2% by weight of said dosage of L-dopa.

8. The method of claim 7, wherein said unit daily dosages of L-dopa and mepiprazole are given in up to 10 fractional dosages.

* * * * *